United States Patent [19]

Jeng

[11] Patent Number: 5,916,882
[45] Date of Patent: Jun. 29, 1999

[54] POVIDONE IODINE (PVP-I) ALCOHOL GEL ANTIMICROBIAL PRE-OPERATIVE SKIN PREPARATION

[75] Inventor: David K. Jeng, Lombard, Ill.

[73] Assignee: Allegiance Corporation, McGaw Park, Ill.

[21] Appl. No.: 08/838,308

[22] Filed: Apr. 8, 1997

[51] Int. Cl.$^6$ .................. A61K 31/715; A61K 31/02; A61K 9/10; A61K 31/74

[52] U.S. Cl. ................. 514/57; 424/78.06; 424/78.07; 424/456; 514/743; 514/944

[58] Field of Search ................. 424/78.06, 78.07, 424/456, 484, 485, 489; 514/743, 887, 944, 54, 57

[56] References Cited

U.S. PATENT DOCUMENTS

| | | | |
|---|---|---|---|
| 4,542,012 | 9/1985 | Dell | 424/58 |
| 4,584,192 | 4/1986 | Dell et al. | 424/81 |
| 4,692,328 | 9/1987 | Kitchell et al. | 424/78 |
| 4,956,170 | 9/1990 | Lee | 424/81 |
| 4,978,527 | 12/1990 | Brink et al. | 424/78 |
| 5,071,648 | 12/1991 | Rosenblatt | 424/78.06 |
| 5,086,606 | 2/1992 | Cole et al. | 536/54 |
| 5,098,717 | 3/1992 | Blackman | 514/648 |
| 5,137,718 | 8/1992 | Gillespie | 424/78.06 |
| 5,173,291 | 12/1992 | Brink et al. | 424/78.06 |
| 5,376,366 | 12/1994 | Petchul et al. | 424/78.07 |
| 5,446,070 | 8/1995 | Mantelle | 514/772.6 |
| 5,529,770 | 6/1996 | McKinzie et al. | 424/78.24 |
| 5,545,401 | 8/1996 | Shanbrom | 424/78.07 |
| 5,547,662 | 8/1996 | Khan et al. | 424/78.03 |
| 5,597,561 | 1/1997 | Kross | 424/78.07 |

FOREIGN PATENT DOCUMENTS

| | | |
|---|---|---|
| 0 640 352 A1 | 1/1995 | European Pat. Off. . |

OTHER PUBLICATIONS

Huang et al. *American Journal of Infection Control*, vol. 22(4): 224–227. Abstract Only, 1994.

Larson et al. *American Journal of Infection Control*, vol. 21(6): 297–301. Abstract Only, 1993.

Hooe et al. *Oral Surgery Oral Medicine Oral Pathology Oral Radiology and Endodontics*, vol. 82(1): 34–37, 1996.

Dieter H.M. Groschel and Timothy L. Pruett, *Surgical Antisepsis*, Disinfection, Sterilization, and Preservation, 4$^{th}$ Edition, Philadelphia, Lea & Fegeger, 1991, pp. 642–654.

*Primary Examiner*—Howard C. Lee
*Attorney, Agent, or Firm*—Michael S. Leonard; Kay H.P. Hannafan

[57] ABSTRACT

The present invention provides antimicrobial skin-preparations useable to disinfect a surgical site for surgery. The antimicrobial skin-preparation formula includes iodine, alcohol and gel. The new pre-operative skin-preparation quickly and effectively kills microorganisms when applied to the surgical site. The skin-preparation continues to effectively inhibit microorganism growth in the applied area over an extended period of time. One gel skin-preparation according to the invention includes alcohol at 60%–90% v/v, iodine at 1.0%–15.0% w/v, and gel at 0.1%–30.0% w/v. A carrier solvent and other optional components may also be added to the formula.

20 Claims, 2 Drawing Sheets

POVIDONE IODINE (PVP-I) ALCOHOL GEL ANTIMICROBIAL PRE-OPERATIVE SKIN PREPARATION

FIELD OF THE INVENTION

The present invention generally relates to antimicrobial pre-operative skin-preparations and more specifically, the present invention relates to povidone iodine (PVP-I) alcohol pre-operative antimicrobial skin-preparations in a gel form.

BACKGROUND OF THE INVENTION

Standard surgical procedures require the surgical site to be disinfected prior to surgery. Effective pre-operative cleansing of the surgical site is critical to reducing the risk of infection to the patient. Pre-operative skin preparation is therefore as important as the prophylactic antibiotic treatment in control of infection.

Microorganisms on the skin can be transient or resident. Transient microorganisms lie on the surface of the skin, while resident microorganisms are found at deeper sites in the skin, for example, in skin hair follicles. During pre-operative procedures it is desirable to initially kill the microorganisms relatively quickly to reduce the length of time to prepare the patient for surgery. It is also important that the antimicrobial activity can be sustained throughout the surgical procedure by the skin-preparation.

Iodophore has been widely used as a disinfectant and as a pre-operative skin preparation. Pre-operative skin-preparation solutions such as PVP-I scrub and paint solutions are commonly used to disinfect the surgical site prior to surgery. Existing iodophore skin-preparation solutions typically include iodine, surfactant and a buffer system to provide appropriate pH in an aqueous system. The solutions typically contain an active ingredient of 7.5% to 10.0% povidone iodine. These concentrations of iodine are desirable to provide effective and extended killing of microorganisms.

Aqueous iodophore skin-preparations tend to run on the patient's body to areas that don't require disinfection. For example, between the patient and the operating table, and may accumulate on those undesired areas where the iodine can cause skin irritation in certain patients. Gel has been added to povidone iodine to reduce running of the skin-preparation. It provides a film texture allowing the antimicrobial to localize at the desirable surgical incision site without reducing the thickness of iodine from the site. Typically, the iodine content of the gel form is about 10.0% w/v or the effect of antimicrobial activity would not be prominent.

Although iodine gel provides the advantage as described, it kills microorganisms at a relative slower rate than other antimicrobial agents such as alcohol. Alcohol has long been recognized as a disinfectant which reduces bacteria, fungi, and some viruses at a great speed. However, alcohol alone evaporates quickly. The disinfection action of alcohol does not continue once the alcohol evaporates from the skin. Accordingly, alcohol alone lacks a prolonged ability to disinfect the surgical site. Iodine skin-preparations are usually applied to a patient in a multi-step process. The typical recommended procedure calls for a 7.5% w/v iodine preparation to be scrubbed on the patient for approximately 2 minutes and then blotted dry. The 7.5% iodine preparation is reapplied to the patient and scrubbed on the patient again for approximately 2 minutes, and blotted dry. A 10.0% w/v iodine solution is then painted onto the patient. During pre-surgical skin-preparation, a shorter time period of application is desirable for practical reasons.

The present invention by adding alcohol to PVP-I gel provides benefits of a rapid and sustained antimicrobial activity, localization of skin-preparation by forming a film on the skin, and a single-step of short time period application. The invention also provides an opportunity to lower the iodine concentration requirement thus reducing the incidence of irritation of certain patients. All these characteristics, in combination, are not described in the precedent skin-preparations.

SUMMARY OF THE INVENTION

The present invention provides povidone iodine alcohol gel antimicrobial skin-preparations useable to disinfect a surgical site for surgery. The new pre-operative skin-preparation quickly and effectively kills microorganisms when applied to the surgical site. The skin-preparation continues to effectively inhibit microorganism growth in the applied area for a relatively long period of time. Application of the skin-preparation is highly controllable because it does not run when applied to a patient. The antimicrobial skin-preparation meets or exceeds the Food and Drug Administration's proposed performance requirement for pre-operative skin-preparations.

The antimicrobial skin-preparation formula includes iodine, alcohol and gel. The concentration of iodine is relatively low compared to existing skin-preparations. However, the new skin-preparation kills microorganisms quickly upon initial application to the skin and continues to kill microorganisms over an extended period of time. The skin-preparation includes an alcohol at 60.0%–90.0% v/v, an iodophor (iodine) at 1.0%–15.0% w/v, and a gel at 0.1%–20.0% w/v. A preferred antimicrobial skin-preparation includes ethanol at 62.0% v/v, povidone iodine at 5.0% w/v, and gel at 7.5% w/v. Other active and enhancing substances such as surfactants can also be included in the formula.

DETAILED DESCRIPTION OF PRESENTLY PREFERRED EMBODIMENTS

Figure 1:
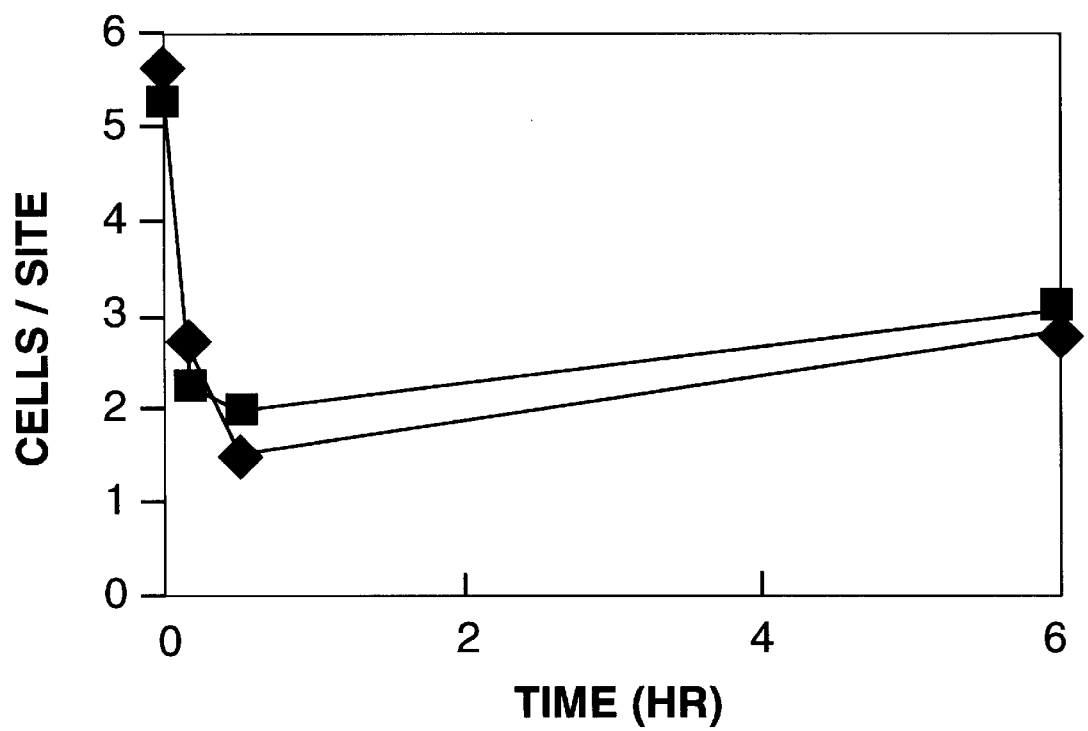
FIG. 1 is a graph showing antimicrobial activity of the present invention PVP-I alcohol gel skin-preparation on normal flora of human inguinal site as described in Example II.

Although the present invention can be made in many different forms, the presently preferred embodiments are described in this disclosure and shown in the attached drawings. This disclosure exemplifies the principles of the present invention and does not limit the broad aspects of the invention only to the illustrated embodiments.

The new pre-operative antimicrobial skin-preparation has a formulation of alcohol, iodine, and gel. The skin-preparation provides rapid and prolonged antimicrobial action. Both transient and resident microorganisms are effectively controlled by the skin-preparation. The skin-preparation is intended to be used for surgery but may also be used for other appropriate applications, for example as a surgical hand wash and general disinfectant. The antimicrobial skin-preparation generally includes alcohol, iodine and gel. The combination of these components provides an initial rapid kill of the microorganisms, a prolonged kill of the resident microorganisms over an extended period of time, and maintains the skin-preparation at the desired localized surgical site to provide a continuous antimicrobial activity at an effective iodine concentration level if not washed off. Because of the initial rapid kill of the microorganisms, only a short amount of time is required to apply the skin-preparation to the patient. The skin-preparation is also relatively mild and minimizes skin irritation.

A presently preferred antimicrobial skin-preparation in accordance with the present invention includes the following components:

| | |
|---|---|
| alcohol | 60.0%–90.0% v/v |
| iodine | 1.0%–15.0% w/v |
| gel | 0.1%–30.0% w/v |

A carrier solvent may be included in the formula to make up 100% of the volume. Other optional components may also be included, for example:

| | |
|---|---|
| base pH adjustor | 0.01%–2.0% w/v |
| acid pH adjustor | 0.01%–5.0% w/v |
| skin irritation reducer | 0.1%–5.0% w/v |

One antimicrobial skin-preparation which has been found to be effective includes the following components:

| | |
|---|---|
| ethyl alcohol | 60.0%–90.0% v/v |
| povidone iodine | 1.0%–15.0% w/v |
| gel | 0.1%–20.0% w/v |

A carrier solvent and other optional components may also be included, for example:

| | |
|---|---|
| sodium hydroxide | 0.01%–2.0% w/v |
| citric acid | 0.01%–5.0% w/v |
| glycerin | 0.1%–5.0% w/v |

One presently preferred formulation of the antimicrobial skin-preparation includes the following components:

| | |
|---|---|
| ethyl alcohol | 62.0% v/v |
| povidone iodine | 5.0% w/v |
| gel | 7.5% w/v |

Optional components may be included, for example:

| | |
|---|---|
| sodium hydroxide | 0.2% w/v |
| citric acid | 0.5% w/v |
| glycerin | 1.0% w/v |

The antimicrobial skin-preparation includes an alcohol as one of the components. The alcohol provides a rapid and effective initial kill of microorganisms. Alcohol rapidly reduces microbial counts once the preparation is applied to the skin and leads iodine to the deeper site of the skin for effective control of resident microorganisms. Alcohols which are suitable for use in health care applications to human skin can be used in the skin-preparation. For example, suitable alcohols include ethyl alcohol, methyl alcohol, isopropyl alcohol, butyl alcohol, propyl alcohol, and other similar alcohols including phenyl alcohol. The concentration of alcohol included in the skin-preparation is selected to provide a rapid, effective initial control of the microorganisms while not being too high to cause instability in the formulation, such as breaking down the gel. Preferably, the amount of alcohol included in the skin-preparation is about 60.0%–90.0% v/v. One presently preferred formulation of the skin-preparation includes ethyl alcohol at about 62.0% v/v.

The antimicrobial skin-preparation includes iodine as one of the components. The iodine provides an effective continued kill of microorganisms. Iodine continues to reduce microbial counts and inhibits microorganisms from growing and repopulating the surgical site. The iodine in the skin-preparation also effectively controls both transient and resident skin inhabiting microorganisms. Preferable iodines for use in the skin-preparation are iodophores (complexes of iodine), and specifically, povidone iodine (PVP-I). Povidone iodine is typically available in a solid powder form and is soluble in an aqueous condition or in a water-alcohol mix. The concentration of povidone iodine in the formulation is selected to provide effective microorganism control over an extended period of time. Preferably, the amount of povidone iodine included in the skin-preparation is about 1.0%–15.0% w/v. One presently preferred formulation of the skin-preparation can have a significantly less concentration of iodine than the concentration in existing pre-operative iodine based skin-preparations, which typically include 7.5%–10.0% w/v iodine. The present inventive skin-preparation surprisingly provides enhanced microorganism control even at relatively lower iodine concentrations. The effective control of microorganisms, both initially and through an extended period, is due to the combination of alcohol, iodine, and gel.

The antimicrobial skin-preparation also includes a gel as one of the components. The gel provides a medium for applying the skin-preparation to the surgical site. The gel gives the skin-preparation a syrup-like consistency and assists in maintaining the microorganism killing agents at the surgical site. The gel formulation reduces running of the skin-preparation by forming a film on the skin and thus, delivers the disinfection action more effectively to the desired skin location. Accordingly, the skin-preparation tends to remain localized at the surgical site where the disinfecting action is needed. The concentration of the iodine can be reduced because the initial action of alcohol enables the skin-preparation to have a lower concentration of iodine in inhibiting the growth of the resident microorganisms. The lower concentration of iodine contributes to less skin irritation.

The gel also reduces the potential for exposing other skin areas on the patient to the skin-preparation. Preferable gels for use in the skin-preparation are water soluble and compatible with the particular alcohol and iodine used in the formulation. The concentration of gel in the formulation is selected to increase the viscosity of the skin-preparation and provide the ability of maintaining the skin-preparation at or close to the desired location on the patient as a film. Preferably, the amount of gel included in the skin-preparation is about 0.1%–20.0% w/v. One preferred formulation of the skin-preparation includes gel at about 7.5% w/v. A preferred gel includes simethicone, hydroxypropylcellulose and nonoxynol-10. The simethicone may be included at about 0.1%–20% w/v of the skin preparation, for example 5.0% w/v of the skin-preparation. The hydroxypropylcellulose may be included at about 0.1%–30% w/v of the skin preparation, for example 2.0% w/v of the skin-preparation. The nonoxynol-10 may be included at about 0.1%–15% w/v of the skin preparation, for example 0.5% w/v of the skin-preparation. Hydrogels may also be suitable for use in the skin-preparation.

The antimicrobial skin-preparation may also include a carrier solvent as one of the components. The carrier solvent provides the balance of the formulation to make 100% of the volume. Suitable carrier solvents are compatible with the particular alcohol, iodine, and gel components in the skin-preparation. A preferable carrier solvent is sterile water.

The antimicrobial skin-preparation formulation may include other components. Acid and base adjusters may be added to maintain a proper pH level. Base pH adjusters can include for example, alkali metal hydroxides. Suitable alkali metal hydroxides include sodium hydroxide and potassium hydroxide, for example. One preferred skin-preparation includes sodium hydroxide at about 0.01%–2.0% w/v of the skin-preparation, and preferably, 0.2% w/v. Acid pH adjusters can include various acids, such as citric acid, lactic acid and acetic acid, for example. One preferred skin-preparation includes citric acid at about 0.01%–5.0% w/v of the skin-preparation, and preferably, 0.5% w/v. The skin-preparation may include skin irritation reducers to reduce the potential for irritating the patient's skin. Suitable skin irritation reducers include glycerin, petroleum jelly, petrolatum, mineral oil, ethylene glycol, and glycerol, for example. One preferred skin-preparation includes glycerin at about 0.1%–5.0% w/v of the skin-preparation, and preferably, 1.0% w/v.

Additional components can also be added to the skin-preparation as desired. For example, a dye could be added to provide a desired color. Fatty acids could be added to lengthen the time of antimicrobial action for an even longer term of protection. Surfactants could also be added to create lather, for example, when the formulation is used as a hand wash.

The antimicrobial gel skin-preparation has been tested and found to effective at rapidly killing microorganisms and inhibiting growth of microorganisms by maintaining its killing action for an extended period of time. The federal Food and Drug Administration ("FDA") has published proposed test methods and performance requirements for healthcare disinfectants, including skin-preparations. The FDA's proposed methods and performance requirements are described in the Tentative Final Monograph for Health-Care Antiseptic Drug Products (the "TFM"). The present antimicrobial skin-preparing has been subjected to the TFM Time-Kill test and Minimum Inhibition Concentration test as discussed in Example I. The present antimicrobial skin-preparation has also been subjected to the TFM efficacy test to evaluate the antimicrobial activity on human skin normal flora for both transient and resident microorganisms using inguinal and abdomen skin testing sites. The skin-preparation meets or exceeds the TFM requirements. Various existing skin-preparation solutions were also tested according to the TFM requirements for comparison to the present gel skin-preparation invention. The gel skin-preparation of the present invention exhibited antimicrobial control equal to or better than the existing solutions.

By way of example, and not limitation, examples of the present invention will now be given:

EXAMPLE I
IN VITRO TIME-KILL TEST AND MINIMUM INHIBITION CONCENTRATION TEST IN EVALUATION OF ANTI-MICROBIAL EFFICACY

An antimicrobial gel skin-preparation according to the present invention was tested for antimicrobial efficacy with the challenge bacteria listed in the FDA's TFM. In addition, the gel skin-preparation was also tested against other bacteria of clinical importance with resistance to various antibiotics. A total of 32 species of microorganisms were used in the tests. Two TFM test methods were conducted in the evaluation of antimicrobial efficacy of the new skin-preparation, specifically, the Time-Kill test and the Minimum Inhibition Concentration test. The skin-preparation contained PVP-I 5% w/v, Ethanol 62% v/v, and gel 7.5% w/v. A control formulation of PVP-I 7.5% w/v, referred to in this example as Betadine, was also tested to provide a comparison to the Prevail skin-preparation.

Principle

It is important that skin-preparations constitute rapid and prolonged antimicrobial action. The Time-Kill test evaluates the rapidity of the antimicrobial action whereas the Minimum Inhibition Concentration assesses the prolonged inhibiting action. The rapidity of the antimicrobial action of the PVP-I alcohol gel skin-preparation was assessed in comparison with the Betadine iodophor control using 15 and 30 seconds of contact in the Time-Kill test. The Minimum Inhibition Concentration test was also conducted to evaluate the long term effectiveness at killing microorganisms. By formulating the PVP-I alcohol gel skin-preparation with PVP-I, alcohol and gel, the antimicrobial action of iodine and alcohol may have synergies or complement each other because of their individual modes of action. The alcohol in the PVP-I alcohol gel formulation enables the antimicrobial skin-preparation to effectively deliver a rapid action against the microorganisms tested and enables the amount of PVP-I to be reduced from a conventional amount of 10% w/v to 5% w/v in the present invention. A lower PVP-I tends to reduce skin irritation caused by the iodophor in certain patients.

Purpose

To comparatively determine the antimicrobial efficacy of PVP-I alcohol gel skin-preparation and a iodophor control (Betadine) in a 15 and 30 seconds Time-Kill test and a Minimum Inhibition Concentration test.

Materials and Methods

A. Samples
1. PVP-I alcohol gel gel skin-preparation (PVP-I 5% w/v, ethanol 62% v/v, gel 7.5% w/v) 4 oz bottle.
2. Control: Betadine PVP-I 7.5% v/v.

B. Methods
1. Time-Kill test: A 1 ml of bacterial culture containing approximately $10^9$/ml bacterial counts was added into 9 ml of the testing products (PVP-I alcohol gel skin-preparation and Betadine control) and mixed vigorously. Samples were taken and transferred to neutralization solution after 15 seconds and 30 seconds exposures. The 15 second and 30 second exposure samples were bioassayed for survival microorganisms by a pour plate method.
2. Minimum Inhibition Concentration test: Equivalent volumes of each of the bacterial cultures was added into each of the testing products (PVP-I alcohol gel skin-preparation and Betadine control) and a series of 1:2 dilution of the mix was made with sterile saline. The mixed materials were incubated for 48 hours to observe the microbial growth.

Results

A. Time-Kill Test: Table I shows that the present invention PVP-I alcohol gel skin-preparation is efficacious to reduce at least 5 log, in 15 seconds, for all testing organisms including those aerobic, anaerobic bacteria and yeasts as proposed by the TFM. The log reduction represents the amount of the organisms killed during the 15 second or 30 second time periods, i.e., the greater the log reduction the greater amount of the organism that was killed. PVP-I alcohol gel gel skin-preparation is also efficacious to reduce the antibiotic resistant organisms with clinical significance. The PVP-I alcohol gel skin-preparation exhibited superior control in antimicrobial activity to the control, particularly with the trend to better control of antibiotic resistant bacterial species.

B. Minimum Inhibition Concentration Test: Table 2 shows that the present invention PVP-I alcohol gel skin-preparation produced similar antimicrobial inhibition activity to the iodophor Betadine control. The concentrations shown in Table 2 represent the minimum concentrations of the PVP-I alcohol gel skin-preparation and the control that limit microbial growth to a TFM specified amount over a 48 hour period.

TABLE 1

Comparative study of PVP-I alcohol gel and iodophor control in microbial Time-Kill test of the organisms listed in the TFM and other antibiotic resistant species in a 15 second and a 30 second exposures.

|  | LOG REDUCTION | | | |
| --- | --- | --- | --- | --- |
|  | 15 sec | | 30 sec | |
|  | PVP-I alcohol gel | Control* | PVP-I alcohol gel | Control* |
| *Staphylococcus aureus* (ATCC#6538) | >8.63 | 7.32 | >8.63 | >8.63 |
| *Staphylococcus aureus* (ATCC#29213) | >5.94 | >5.94 | >5.94 | >5.94 |
| *Staphylococcus aureus* (ATCC #33591) M,V** | >6.07 | 2.11 | >6.07 | 4.27 |
| *Staphylococcus aureus* (ATCC # 33592) G,M** | >6.15 | 2.24 | >6.15 | >6.15 |
| *Staphylococcus aureus* (ATCC # 33593) G,M** | >5.71 | >5.71 | >5.71 | >5.71 |
| *Staphylococcus aureus* (ATCC # 33594) G** | >6.03 | >6.03 | >6.03 | >6.03 |
| *Staphylococcus aureus* (ATCC # 43300) M** | >5.78 | 2.90 | >5.78 | >5.78 |
| *Staphylococcus epidermidis* (ATCC # 12228) | >5.40 | >5.40 | >5.40 | >5.40 |
| *Staphylococcus epidermidis* (ATCC # 51624) M** | >5.75 | 2.86 | >5.40 | 2.89 |
| *Staphylococcus epidermidis* (ATCC # 51625) M** | >5.33 | >5.33 | >5.33 | >5.33 |
| *Staphylococcus haemolyticus* (ATCC # 29970) | >5.13 | 2.15 | >5.13 | >5.13 |
| *Staphylococcus hominis* (ATCC#25615) | >5.22 | 1.79 | >5.22 | >5.22 |
| *Staphylococcus saprophyticus* (ATCC#15305) | >5.55 | 2.26 | >5.55 | >5.55 |
| *Streptococcus pyogenes* (ATCC#12351) | >4.51 | >4.51 | >4.51 | >4.51 |
| *Streptococcus pneumoniae* (ATCC#35088) | >4.37 | 3.06 | >4.37 | >4.37 |
| *Micrococcus lureus* (ATCC#7468) | >4.56 | >4.56 | >4.56 | >4.56 |
| *Enterococcus faecalis* (ATCC#29212) | >5.98 | >5.98 | >5.98 | >5.98 |
| *Enterococcus faecalis* (ATCC #51575) G,S,V** | >6.04 | 4.63 | >6.04 | >6.04 |
| *Enterococcus faecium* (ATCC#49224) | >5.61 | 3.84 | >5.61 | 4.97 |
| *Acinetobacter anitratus* (ATCC#49137) | >5.42 | >5.42 | >5.42 | >5.42 |
| *Enterobacter cloacae* (ATCC#13047) | >5.98 | >5.98 | >5.98 | >5.98 |
| *Eschericia coli* (ATCC#11229) | >7.66 | >7.66 | >7.66 | >7.66 |
| *Eschericia coli* (ATCC#25922) | >5.82 | >5.82 | >5.82 | >5.82 |
| *Klebsiella pneumoniae* (ATCC#27736) | >5.58 | 4.02 | >5.58 | >5.58 |
| *Klebsiella oxytoca* (ATCC#15764) | >5.70 | >5.70 | >5.70 | >5.70 |
| *Proteus mirabilis* (ATCC#4630) | >6.11 | >6.11 | >6.11 | >6.11 |
| *Pseudomonas aeruginosa* (ATCC#15442) | >6.02 | >6.02 | >6.02 | >6.02 |
| *Pseudomonas aeruginosa* (ATCC#27853) | >5.81 | >5.81 | >5.81 | >5.81 |
| *Serratia marcescens* (ATCC#14756) | >5.95 | >5.95 | >5.95 | >5.95 |
| *Bacteroides fragilis* (ATCC#25285) | >5.54 | 4.81 | >5.54 | >5.54 |
| *Cadida albicans* (ATCC#10231) | >7.58 | 2.04 | >7.58 | 5.00 |
| *Candida tropicalis* (ATCC#750) | 3.23 | 1.82 | >5.54 | 3.35 |

*Betadine PVP-I (7.5%).
**Resistance in: M = Methicillin; G = Gentamicin; S = Streptomycin; V = Vancomycin

TABLE 2

Comparative study of PVP-I alcohol gel and iodophor control in Minimum Inhibition Concentration test with the organisms listed in the TFM and other antibiotic resistant species.

|  | Minimum Inhibition Concentration* | |
| --- | --- | --- |
|  | PVP-I alcohol gel | Control** |
| *Staphylococcus aureus* (ATCC#6538) | 1:128 | 1:32 |
| *Staphylococcus aureus* (ATCC#29213) | 1:32 | 1:32 |
| *Staphylococcus aureus* (ATCC #33591) M,V*** | 1:64 | 1:64 |
| *Staphylococcus aureus* (ATCC # 33592) G,M*** | 1:128 | 1:32 |
| *Staphylococcus aureus* (ATCC # 33593) G,M*** | 1:64 | 1:64 |
| *Staphylococcus aureus* (ATCC # 33594) G*** | 1:64 | 1:64 |
| *Staphylococcus aureus* (ATCC # 43300) M*** | 1:64 | 1:64 |
| *Staphylococcus epidermidis* (ATCC # 12228) | 1:64 | 1:64 |

TABLE 2-continued

Comparative study of PVP-I alcohol gel and iodophor control in Minimum Inhibition Concentration test with the organisms listed in the TFM and other antibiotic resistant species.

| | Minimum Inhibition Concentration* | |
|---|---|---|
| | PVP-I alcohol gel | Control** |
| *Staphylococcus epidermidis* (ATCC # 51624) M*** | 1:32 | 1:32 |
| *Staphylococcus epidermidis* (ATCC # 51625) M*** | 1:64 | 1:64 |
| *Staphylococcus haemolyticus* (ATCC # 29970) | 1:64 | 1:64 |
| *Staphylococcus hominis* (ATCC#25615) | 1:128 | 1:32 |
| *Staphylococcus saprophyticus* (ATCC#15305) | 1:128 | 1:32 |
| *Streptococcus pyogenes* (ATCC#12351) | 1:32 | 1:16 |
| *Streptococcus pneumoniae* (ATCC#35088) | 1:64 | 1:128 |
| *Micrococcus lureus* (ATCC#7468) | 1:32 | 1:32 |
| *Enterococcus faecalis* (ATCC#29212) | 1:32 | 1:32 |
| *Enterococcus faecalis* (ATCC#51575) G,S,V*** | 1:32 | 1:32 |
| *Enterococcus faecium* (ATCC#49224) | 1:64 | 1:32 |
| *Acinetobacter anitratus* (ATCC#49137) | 1:16 | 1:32 |
| *Enterobacter cloacae* (ATCC#13047) | 1:16 | 1:32 |
| *Eschericia coli* (ATCC#11229) | 1:16 | 1:32 |
| *Eschericia coli* (ATCC#25922) | 1:64 | 1:32 |
| *Klebsiella pneumoniae* (ATCC#27736) | 1:16 | 1:32 |
| *Klebsiella oxytoca* (ATCC#15764) | 1:16 | 1:32 |
| *Proteus mirabilis* (ATCC#4630) | 1:32 | 1:32 |
| *Pseudomonas aeruginosa* (ATCC#15442) | 1:32 | 1:32 |
| *Pseudomonas aeruginosa* (ATCC#27853) | 1:32 | 1:16 |
| *Serratia marcescens* (ATCC#14756) | 1:16 | 1:32 |
| *Bacteroides fragilis* (ATCC#25285) | 1:32 | 1:16 |
| *Candida albicans* (ATCC#10231) | 1:64 | 1:32 |
| *Candida tropicalis* (ATCC#750) | 1:16 | 1:32 |

*Dilution from the original concentration.
**Betadine PVP-I (7.5%).
***Resistance in: M = Methicillin; G = Gentamicin; S = Streptomycin; V = Vancomycin

EXAMPLE II
CLINICAL ANTIMICROBIAL EFFICACY DETERMINATION ON NORMAL FLORA OF HUMAN SKIN

An antimicrobial gel skin-preparation according to the present invention was also tested for antimicrobial efficacy on normal flora of human skin as specified in the FDA's TFM. The new PVP-I alcohol gel skin-preparation formulation was subjected to a vigorous efficacy test to evaluate the antimicrobial activity on human skin normal flora for both transient and resident microorganisms using inguinal and abdomen skin testing sites. The PVP-I alcohol gel skin-preparation contained PVP-I 5% w/v, Ethanol 62% v/v, and gel 7.5% w/v. A control formulation of PVP-I 10.0% w/v, referred to in this example as Betadine, was also tested to provide a comparison to the PVP-I alcohol gel skin-preparation.

Principle

The TFM proposes that the efficacy is measured on human inguinal and abdomen skin sites for the reduction of normal microbial flora. Ten minutes after the application, a minimum of three-log reduction from a baseline of at least $10^5$ cells per site in inguinal area and a two-log reduction from a baseline of at least $10^3$ cells per site in abdomen area are required. The survival organisms shall not grow to greater than the baseline level in 6 hours after the application. The action of the new PVP-I alcohol gel skin-preparation and the comparison formulations were evaluated in single applications of 30 seconds. The Betadine control was tested at a 5 minute application.

Purpose

To comparatively determine the antimicrobial efficacy in a 30-second-one-time application of the present invention versus a 5 minute application of a traditional Betadine iodophor solution control.

Materials
A. Samples
1. PVP-I alcohol gel skin-preparation (PVP-I 5% w/v, ethanol 62% v/v, gel) 4 oz bottle.
2. Control: Betadine PVP-I 10% v/v solution (iodophor solution).

B. Subjects
1. Number: Twelve (12) randomly selected human volunteers of both sexes.
2. Age: Between 18 to 70 with healthy skin.
3. Subjects were pre-screened to exhibit a microbial baseline of $10^5$ and $10^3$ organisms per inguinal and abdomen testing site, respectively.

Protocol
A. Before Treatment
1. A two-week wash off time is assigned to subjects without the use of products containing antimicrobial agents.
2. A baseline sample is taken from randomized testing sites with stripping solution containing neutralizer according to the method described in the TFM.
3. The present invention PVP-I alcohol gel formulation is applied onto test sites, scrubbing in a circular motion with a sponge for 30 seconds or 1 minute. The control Betadine solution is similarly applied for 5 minutes and replenished when dry.

B. After Treatment
1. At 10 minutes, 30 minutes and 6 hours post-application, samples were taken from randomized test sites according to the method described in the TFM using a striping solution containing an appropriate neutralizer.
2. Samples were assayed for survival colonies by the agar pour plate method.

Results

Figure 2:
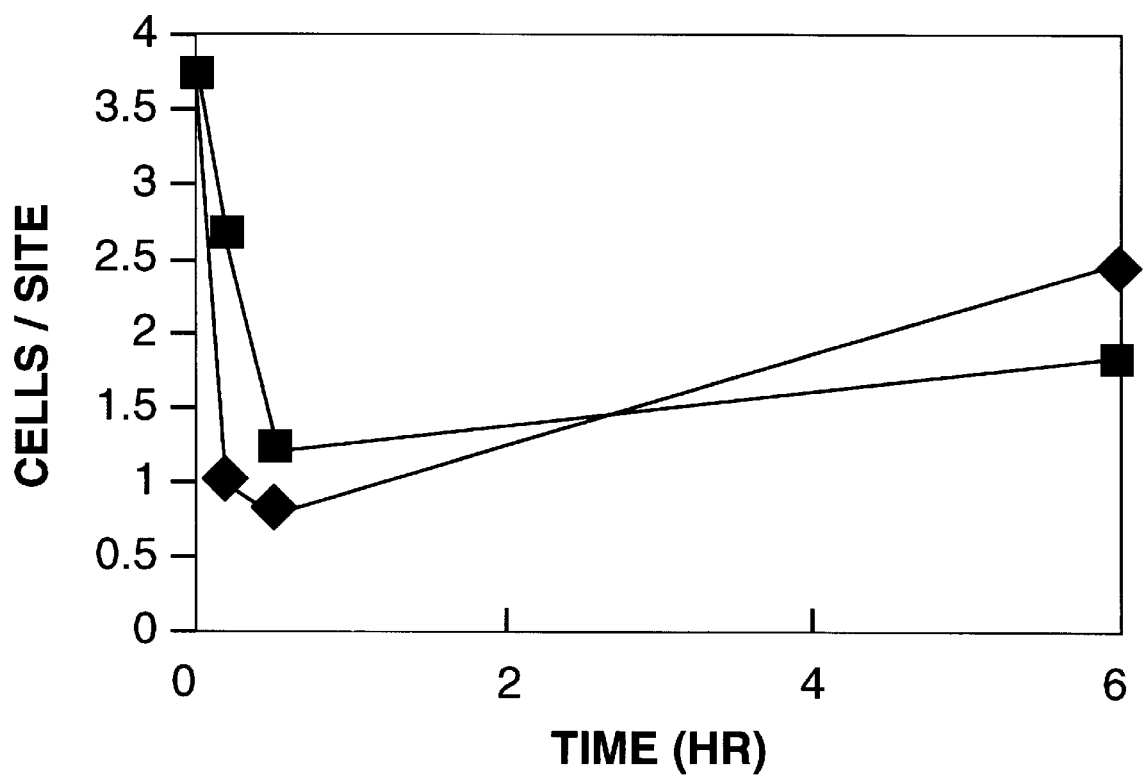
FIG. 2 is a graph showing antimicrobial activity of the present invention PVP-I alcohol gel skin-preparation on normal flora of human skin abdomen site as described in Example II.

Tables 3 and 4 show that the present invention PVP-I alcohol gel skin-preparation in a 30 second one step application satisfied the requirements specified by the TFM in inguinal (groin) (Table 3) and abdomen (Table 4) testing sites. The new skin-preparation reduced at least 3 logs of normal flora in 10 minutes post-application and the microbial level did not rise to greater than the baseline in 6 hours. The log reduction numbers represent the amount of normal flora killed or reduced below the baseline. Accordingly, a 1 log reduction drop below the baseline indicates a 90% kill, a 2 log reduction drop below the baseline indicates a 99% kill, and a 3 log drop below the baseline indicates a 99.9% kill, etc. FIGS. 1 and 2 graphically show the test results of the performance of the PVP-I alcohol gel formulation and the Betadine control solution. FIG. 1 shows antimicrobial activity of PVP-I alcohol gel skin-preparation vs. Betadine control on normal flora of human inguinal site: Series 1=PVP-I alcohol gel (30 sec application time); Series 2=Betadine control (5 min application time). FIG. 2 shows antimicrobial activity of PVP-I alcohol gel skin-preparation vs. Betadine control on normal flora of human abdomen site: Series 1=PVP-I alcohol gel (30 sec application time); Series 2=Betadine control (5 min application time). As can be seen in Tables 3 and 4, the present invention exhibited superior performance as compared to the 62% ethanol gel and the 5% PVP-I gel alone for both the inguinal and abdomen tests. The PVP-I alcohol gel skin-preparation of the present invention had a greater log reduction (greater microorganism kill) than the other two gels after 10 minutes, 30 minutes and 6 hours.

TABLE 3

Antimicrobial activity of the PVP-I alcohol gel skin-preparation at inguinal site in comparison with ethanol gel and PVP-I gel using Betadine PVP-I (10%) as a control.

| Sample | Time | Baseline | Log Reduction per Inguinal Site | | |
|---|---|---|---|---|---|
| | | | 10 mi | 30 min | 6 hr |
| PVP-I alcohol gel | 30 sec | 5.656 | 2.950 | 4.141 | 2.784 |
| 62% Ethanol Gel | 30 sec | 5.396 | 2.274 | 1.581 | 0.546 |
| 5% PVP-I Gel | 30 sec | 5.396 | 2.272 | 1.372 | 0.686 |
| Betadine | 5 min | 5.339 | 3.053 | 3.352 | 2.247 |

TABLE 4

Antimicrobial activity of the PVP-I alcohol gel skin-preparation at abdomen site in comparison with ethanol gel and PVP-I gel using Betadine PVP-I (10%) as a control.

| Sample | Time | Baseline | Log Reduction per Abdomen Site | | |
|---|---|---|---|---|---|
| | | | 10 min | 30 min | 6 hr |
| PVP-I alcohol gel | 30 sec | 3.748 | 2.692 | 2.937 | 1.393 |
| 62% Ethanol Gel | 30 sec | 3.928 | 1.990 | 1.669 | 0.059 |
| 5% PVP-I Gel | 30 sec | 3.928 | 2.018 | 1.404 | 0.136 |
| Betadine | 5 min | 3.774 | 1.098 | 2.565 | 1.941 |

EXAMPLE III
EXAMPLE OF MAKING THE PRESENT INVENTION

The presently preferred method of making the PVP-I alcohol gel skin-preparation includes slowly combining the solid PVP-I alcohol gel components with the liquid alcohol. The components are mixed as they are combined. For example, one method of making a 100 ml amount of the skin-preparation will now be described.

A test batch of the skin-preparation is made. The desired amounts of PVP-I (e.g., 5.0% w/v), and gel (e.g., 7.5% w/v) are measured and added to a mixing container. Ethyl alcohol is added while mixing until the total volume of 100 ml is obtained. The volume of ethyl alcohol required to make 100 ml of the skin-preparation is noted. Another batch of the skin-preparation is made by placing the amount of alcohol noted in the test batch in a mixing container. The PVP-I and gel components are slowly added to the ethyl alcohol while mixing. The resultant formulation will contain 100 ml of the present invention PVP-I alcohol gel skin-preparation.

The antimicrobial skin-preparation can be used as follows. The desired area to be treated on the patient is selected. The skin-preparation in gel form is applied to the selected area and the area is scrubbed with the skin-preparation. Due to the rapid antimicrobial action of the skin-preparation, the selected area need only be scrubbed for approximately 30 seconds which shortens the amount of time needed for pre-operative procedures. The skin-preparation has been found to be effective in reducing the skin normal flora in 30 seconds. The skin-preparation tends to remain confined to the local area in which it is applied and continues to provide effective killing of microorganisms for an extended period of time. The skin-preparation is water soluble and thus, it is easily cleaned from the patient after surgical operation.

While the presently preferred embodiments have been illustrated and described, numerous changes and modifications can be made without significantly departing from the spirit and scope of this invention. Therefore, the inventor intends that such changes and modifications are covered by the appended claims.

The invention is claimed as:

1. An antimicrobial formulation comprising:
   alcohol from about 60.0% v/v to about 90.0% v/v of the formulation;
   iodine from about 1.0% w/v to about 15.0% w/v of the formulation; and
   gel from about 0.1% w/v to about 20.0% w/v of the formulation.

2. The antimicrobial formulation of claim 1 wherein the alcohol is selected from the group consisting of ethyl alcohol, methyl alcohol, isopropyl alcohol, butyl alcohol and propyl alcohol.

3. The antimicrobial formulation of claim 1 wherein the iodine is povidone iodine.

4. The antimicrobial formulation of claim 1 wherein the gel is a water soluble gel.

5. The antimicrobial formulation of claim 1 wherein the alcohol is about 62% v/v of the formulation.

6. The antimicrobial formulation of claim 1 wherein the iodine is about 5% w/v of the formulation.

7. The antimicrobial formulation of claim 1 wherein the gel is about 7.5% w/v of the formulation.

8. The antimicrobial formulation of claim 1 wherein the gel simethicone from about 0.1% w/v to about 20% w/v of the formulation; and
   hydroxypropylcellulose from about 0.1% w/v to about 30% w/v of the formulations.

9. The antimicrobial formulation of claim 1 further comprising a base pH adjuster from about 0.01% w/v to about 2% w/v of the formulation.

10. The antimicrobial formulation of claim 9 wherein the base pH adjuster is an alkali metal hydroxide.

11. The antimicrobial formulation of claim 1 further comprising an acid pH adjuster from about 0.01% w/v to about 5% w/v of the formulation.

12. The antimicrobial formulation of claim 1 further comprising a skin irritation reducer from about 0.1% w/v to about 5% w/v of the formulation.

13. The antimicrobial formulation of claim 12 wherein the skin irritation reducer is selected from the group consisting of glycerin, petroleum jelly, petrolatum, mineral oil, ethylene glycol and glycerol.

14. An antimicrobial formulation comprising:

ethyl alcohol from about 60.0% v/v to about 90.0% v/v of the formulation;

povidone iodine from about 1.0% w/v to about 15.0% w/v of the formulation; and gel from about 0.1% w/v to about 20.0% w/v of the formulation.

15. The antimicrobial formulation of claim 14 further comprising:

a base pH adjuster from about 0.01% w/v to about 2% w/v of the formulation;

an acid pH adjuster from about 0.01% w/v to about 5% w/v of the formulation; and a skin irritation reducer from about 0.1% w/v to about 5% w/v of the formulation.

16. An antimicrobial formulation comprising:

ethyl alcohol at about 62.0% v/v of the formulation;

povidone iodine at about 5.0% w/v of the formulation; and gel at about 7.5% w/v of the formulation.

17. The antimicrobial formulation of claim 16 further comprising:

sodium hydroxide at about 0.2% w/v of the formulation;

citric acid at about 0.5% w/v of the formulation; and glycerin at about 1.0% w/v of the formulation.

18. A method of applying a pre-operative skin preparation to a patient comprising the steps of:

a) providing a skin-preparation formulation comprising:

alcohol from about 60.0% v/v to about 90.0% v/v of the formulation;

iodine from about 1.0% w/v to about 15.0 w/v of the formulation; and gel from about 0.1% w/v to about 20.0% w/v of the formulation;

b) applying the skin-preparation formulation to a surgical site on the patient; and c) removing any excess amount of the skin-preparation formulation from the surgical site.

19. The method of claim 18 wherein step b) comprises the step of scrubbing the surgical site with the skin-preparation formulation for approximately a 30 second maximum length of time.

20. The method of claim 18 wherein step a) comprises the step of providing the skin-preparation formulation comprising ethyl alcohol from about 60.0% v/v to about 90.0% v/v of the formulation;

povidone iodine from about 1.0% w/v to about 15.0 w/v of the formulation; and gel from about 0.1% w/v to about 20.0% w/v of the formulation.

* * * * *